United States Patent [19]

Kazmaier et al.

[11] Patent Number: 4,751,327
[45] Date of Patent: * Jun. 14, 1988

[54] PHOTOCONDUCTIVE IMAGING MEMBERS WITH UNSYMMETRICAL SQUARAINE COMPOUNDS

[75] Inventors: Peter M. Kazmaier; Richard A. Burt; Giuseppa Baranyi, all of Mississauga, Canada

[73] Assignee: Xerox Corporation, Stamford, Conn.

[*] Notice: The portion of the term of this patent subsequent to Nov. 12, 2002 has been disclaimed.

[21] Appl. No.: 914,218

[22] Filed: Oct. 2, 1986

Related U.S. Application Data

[62] Division of Ser. No. 749,857, Jun. 28, 1985, Pat. No. 4,624,904.

[51] Int. Cl.[4] .................. C07C 85/00; C07C 85/02; C07C 85/06
[52] U.S. Cl. .................................................. 564/307
[58] Field of Search ......................................... 564/307

[56] References Cited

U.S. PATENT DOCUMENTS

| | | | |
|---|---|---|---|
| 4,521,621 | 6/1985 | Yanus et al. | 564/307 |
| 4,523,035 | 6/1985 | Yanus | 564/307 |
| 4,524,218 | 6/1985 | Baranyi et al. | 564/307 |
| 4,525,592 | 6/1985 | Law et al. | 564/307 |
| 4,552,822 | 11/1985 | Kazmaier et al. | 564/307 X |
| 4,585,895 | 4/1986 | Law | 564/307 |
| 4,621,038 | 11/1986 | Kazmaier et al. | 564/307 X |
| 4,626,485 | 12/1986 | Kin et al. | 564/307 X |

Primary Examiner—Paul F. Shaver
Attorney, Agent, or Firm—E. O. Palazzo

[57] ABSTRACT

Disclosed are unsymmetrical squaraine compounds of the following formula

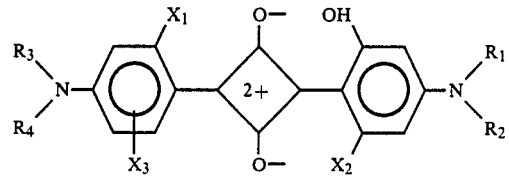

wherein $R_1$, $R_2$, $R_3$ and $R_4$ are independently selected from the group consisting of alkyl, aryl, heterocyclic, benzyl, and halobenzyl; and $X_1$, $X_2$ and $X_3$ are independently selected from the group consisting of hydrogen, alkyl, halogen, carboxy, and hydroxy; and photoresponsive imaging members having incorporated therein the aforementioned squaraine compounds.

16 Claims, 2 Drawing Sheets

PHOTOCONDUCTIVE IMAGING MEMBERS WITH UNSYMMETRICAL SQUARAINE COMPOUNDS

This is a division of application Ser. No. 749,857, filed June 28, 1985, now U.S. Pat. No. 4,624,904.

BACKGROUND OF THE INVENTION

This invention is generally directed to squaraine compositions of matter, and the incorporation thereof into layered photoresponsive imaging members. More specifically, the present invention encompasses layered photoresponsive imaging members having incorporated therein as photogenerating pigments the unsymmetrical squaraine compounds illustrated hereinafter. Accordingly, in one embodiment of the present invention the photoresponsive imaging member, which is sensitive to visible and/or infrared wavelengths, is comprised of a photoconductive or photogenerating layer containing the unsymmetrical squaraine compounds illustrated hereinafter, and an aryl amine hole transport layer. Moreover, included within the scope of the present invention are imaging members which are responsive to visible light, and infrared illumination needed for laser printing, which members comprise, for example, in addition to an unsymmetrical squaraine photoconductive layer and an aryl amine hole transport layer, a photogenerating layer.

Numerous different xerographic photoconductive members are known including, for example, a homogeneous layer of a single material such as vitreous selenium, or a composite layered device with a dispersion of a photoconductive composition. An example of one type of composite xerographic photoconductive member is described in U.S. Pat. No. 3,121,006 wherein there is disclosed finely divided particles of a photoconductive inorganic compound dispersed in an electrically insulating organic resin binder. One member comprises, coated on a paper backing, a binder layer with particles of zinc oxide uniformly dispersed therein. The binder materials disclosed in this patent comprise a material such as polycarbonate resins, polyester resins, and polyamide resins, which are incapable of transporting for any significant distance injected charge carriers generated by the photoconductive particles. As a result the photoconductive particles must be in a substantially contiguous particle to particle contact throughout the layer to permit charge dissipation required for a cyclic operation. Accordingly, a relatively high concentration, about 50 percent by volume, of photoconductive material is usually necessary to obtain sufficient photoconductor particle to particle contact for rapid discharge. This high photoconductive loading can destroy the physical continuity of the resinous binder, and thus significantly reduce the mechanical properties thereof. There are also known photoreceptors comprised of inorganic or organic materials wherein the charge carrier generating, and charge carrier transport functions are accomplished by discrete contiguous layers. Additionally, layered photoreceptor materials are disclosed in the prior art which include an overcoating layer of an electrically insulating polymeric material.

Recently, there has been disclosed specific layered photoresponsive devices comprised of separate generating and transport layers, reference U.S. Pat. No. 4,265,990; and overcoated photoresponsive members with a hole injecting layer, a hole transport layer, a photogenerating layer, and a top coating of an insulating organic resin, reference U.S. Pat. No. 4,251,612. The disclosures of each of these patents are totally incorporated herein by reference.

Many other patents are in existence describing layered photoresponsive layered devices with generating substances, such as U.S. Pat. No. 3,041,167, which discloses an overcoated imaging member containing a conductive substrate, a photoconductive layer, and an overcoating layer of an electrically insulating polymeric material. This member is utilized in an electrophotographic copying method by, for example, initially charging with an electrostatic potential of a first polarity, imagewise exposing, and subsequently effecting development thereof. Prior to each succeeding imaging cycle, the member can be charged with an electrostatic charge of a second opposite polarity. Sufficient additional charges of the second polarity are applied so as to create across the member a net electrical field. Simultaneously, mobile charges of the first polarity are created in the photoconductive layer by applying an electrical potential to the substrate. The imaging potential which is developed to form the visible image is present across the photoconductive layer and the overcoating layer.

There is also disclosed in Belgian Pat. No. 763,540 an electrophotographic member having at least two electrically operative layers, the first comprising a photoconductive layer which is capable of photogenerating charge carriers, and injecting these carriers into a continuous active layer containing an organic transporting material which is substantially nonabsorbing in the spectral region of intended use, and permits the injection of photogenerated holes from the photoconductive layer. Additionally, there is disclosed in U.S. Pat. No. 3,041,116 a photoconductive material with a transparent plastic material overcoated on a layer of vitreous selenium present on a substrate.

Furthermore, there is disclosed in U.S. Pat. Nos. 4,232,102 and 4,233,383 photoresponsive imaging members comprised of trigonal selenium doped with sodium carbonate, sodium selenite, and trigonal selenium doped with barium carbonate; and barium selenite or mixtures thereof. Moreover, there is disclosed in U.S. Pat. No. 3,824,099 certain photosensitive hydroxy squaraine compositions. According to the disclosure of this patent, the squaraine compositions are photosensitive in normal electrostatographic imaging systems.

Also, there is illustrated in U.S. Pat. No. 4,415,639, the disclosure of which is totally incorporated herein by reference, the use of hydroxy squaraines as a photoconductive layer in an infrared sensitive photoresponsive device. More specifically, there is described in this patent an improved photoresponsive device comprised of a substrate, a hole blocking layer, an optional adhesive interfacial layer, an inorganic photogenerating layer, a hydroxy squaraine photoconductive composition capable of enhancing or reducing the intrinsic properties of the photogenerating layer, and a hole transport layer.

Additionally, there is disclosed in U.S. Pat. No. 4,471,041, the disclosure of which is totally incorporated herein by reference, the use of novel julolidinyl squaraine compositions as photoconductive substances in photoresponsive devices which are sensitive to infrared light, and/or visible illumination. As indicated in the above-mentioned patent, the improved photoresponsive device in one embodiment is comprised of a supporting substrate, a hole blocking layer, an optional adhesive interfacial layer, an inorganic photogenerating layer, a photoconducting composition capable of enhancing or reducing the intrinisic properties of the photogenerating layer, which composition is comprised of the novel julolidinyl squaraine compositions disclosed therein, and a hole transport layer.

There is further disclosed in U.S. Pat. No. 4,486,520 photoresponsive imaging members with photogenerating layers of certain fluorinated squaraine compositions. Examples of specific fluorinated squaraines disclosed include bis(4-dimethylamino-2-fluorophenyl)squaraine, bis(4-[N,N,diethylamino-2-fluorophenyl])squaraine, bis(4-[N-methyl-N-ethyl-2-fluoroaniline])squaraine, bis(4-[N,N-dibenzyl-2-fluoroaniline])squaraine, bis(4-[N-methyl-N-benzyl-2-fluoroaniline])squaraine, and bis(4-[N-ethyl-N-benzyl-2-fluoroaniline])squaraine. Other useful fluorinated squaraine compositions include bis(4-[N,N,-di(4-chlorophenylmethyl)-2-fluorophenyl])squaraine, bis(4-[N-methyl-N-(4-chlorophenylmethyl)-2-fluorophenyl])squaraine, and bis(4-[N-benzyl-N-(-chlorophenylmethyl)-2-fluorophenyl])-squaraine. The disclosure of this patent is totally incorporated herein by reference.

There is also illustrated in a copending application U.S. Ser. No. 557,795 entitled Novel Squaraine Systems, the disclosure of which is totally incorporated herein by reference, photoresponsive imaging members with unsymmetrical squaraines similar to those of the present application. More specifically, there is disclosed in this patent application a process for synthesizing an unsymmetrical squaraine comprising forming a mixture of squaric acid, a primary alcohol having a boiling point between 150° C. and about 190° C., a first tertiary amine having the formula:

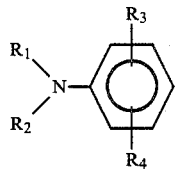

and a second tertiary amine having the formula:

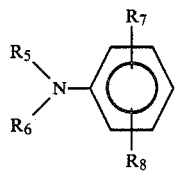

wherein $R_1$, $R_2$, $R_5$ and $R_6$ are independently selected from the group consisting of alkyl radicals having from 1 to 4 carbon atoms, phenyl radicals and radicals having the formula:

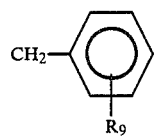

and $R_3$, $R_4$, $R_7$ and $R_8$ are independently selected from the group consisting of H, $CH_3$, $CH_2CH_3$, $CF_3$, F, Cl, Br, and COOH wherein at least one of $R_3$ and $R_4$ are different than $R_7$ and $R_8$ if $R_7$ and $R_8$ are located on the same relative position on the aromatic ring as $R_3$ and $R_4$;

and wherein $R_9$ is selected from the group consisting of H, alkyl radicals having from 1 to 4 carbon atoms, F, Cl, Br, COOH, CN and $CF_3$; and heating the mixture at a temperature below the boiling points of the alcohol, the first tertiary amine and the second tertiary amine.

Furthermore, there is disclosed in copending application U.S. Ser. No. 650,380, the disclosure of which is totally incorporated herein by reference, entitled Processes for the Preparation of Mixed Squaraine Compositions, other unsymmetrical squaraines. Specifically, there is illustrated in this application a mixed squaraine composition comprised of the following three components

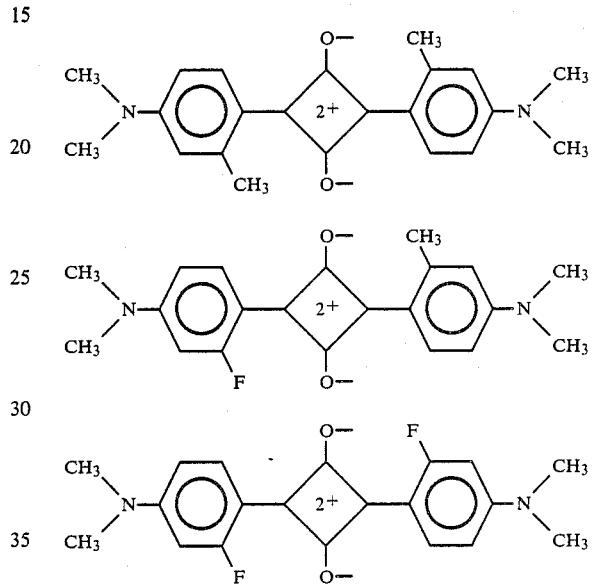

Nevertheless, there continues to be a need for new squaraine compounds which are useful in photoconductive imaging members. Also, there continues to be a need for photoresponsive imaging members comprised of unsymmetrical squaraine compounds. Further, there is a need for layered unsymmetrical squaraine photoresponsive imaging members that are sensitive to a broad range of wavelengths, and more specifically are sensitive to infrared light and visible light thereby permitting their use in a number of imaging and printing systems. Moreover, there continues to be a need for imaging members with unsymmetrical squaraine compounds which can be repeatedly used in a number of imaging cycles without deterioration thereof from the machine environment or surrounding conditions. There also continues to be a need for specific unsymmetrical squaraine photogenerating pigments with a hydroxy substituent thereon, which simultaneously possess higher photosensitivity than closely related squaraines, low dark decay properties, and high charge acceptance values thereby permitting images of excellent resolution with minimum background deposits to be obtained. Another need resides in providing layered photoresponsive imaging members with unsymmetrical squaraine compounds, photogenerating pigments, and aryl amine hole transport molecules.

SUMMARY OF THE INVENTION

It is therefore an object of the present invention to provide unsymmetrical squaraine compositions of matter useful for incorporation into photoconductive imaging members.

In another object of the present invention there are provided layered panchromatic photoresponsive imaging members sensitive to visible light as well as infrared light, and comprised of unsymmetrical squaraine compounds.

A further specific object of the present invention resides in the provision of an improved overcoated photoresponsive imaging member comprised of a photoconductive layer containing unsymmetrical squaraine compounds, and a hole transport layer containing therein aryl amine molecules.

A further object of the present invention resides in photoresponsive imaging members with a photoconductive layer comprised of the unsymmetrical squaraine compounds illustrated hereinafter situated between an aryl amine hole transport layer and a photogenerating layer.

Another object of the present invention resides in the provision of improved photoresponsive imaging members with a photogenerating composition situated between an aryl amine hole transport layer and a photoconductive layer comprised of the unsymmetrical squaraine compounds described herein, which members are simultaneously responsive to infrared light and visible light.

In yet still another object of the present invention there are provided overcoated photoresponsive imaging members simultaneously responsive to infrared light, and visible light comprised of a photoconductive layer containing therein the unsymmetrical squaraine compounds illustrated situated between an aryl amine hole transport layer and a layer comprised of a photogenerating composition.

Additionally, another object of the present invention resides in the provision of imaging and printing methods with the photoresponsive imaging members described hereinafter.

Further, another object of the present invention resides in processes for obtaining in high yields unsymmetrical squaraine compounds.

Additionally, in a further object of the present invention the are provided unsymmetrical hydroxy squaraine compounds sensitive to visible and infrared wavelengths which simultaneously possess high photosensitivity, low dark decay properties, and superior charge acceptance values.

These and other objects of the present invention are accomplished by providing unsymmetrical squaraine compounds of the following formula:

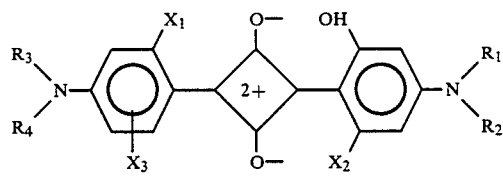

wherein $R_1$, $R_2$, $R_3$, and $R_4$ are independently selected from the group consisting of alkyl, aryl, heterocyclic, benzyl, and halobenzyl; and $X_1$, $X_2$ and $X_3$ are independently selected from the group consisting of hydrogen, alkyl, halogen, carboxy, and hydroxy, subject to the provision that $X_2$ and $X_3$ represent different, that is not the same, substituents. Heterocyclic substituents include pyrrols, quinolines, and indoles. Halo substituents are chloride, fluoride, bromide, and iodide, with fluoride and chloride being especially preferred.

Alkyl substituents include those of from 1 to about 20 carbon atoms, such as methyl, ethyl, propyl, butyl, pentyl, hexyl and pentadecyls, with lower alkyl of from about 1 to 6 carbon atoms being preferred. Examples of aryl substituents are those with from about 6 to about 24 carbon atoms inclusive of phenyl and naphthyl.

Illustrative examples of unsymmetrical squaraine compounds included within the scope of the present invention are:

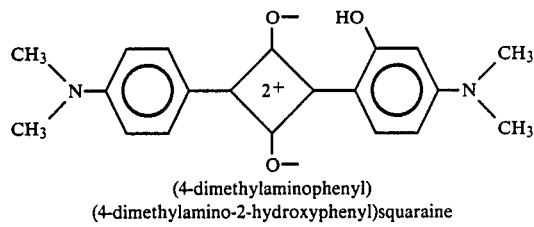

(4-dimethylaminophenyl)
(4-dimethylamino-2-hydroxyphenyl)squaraine

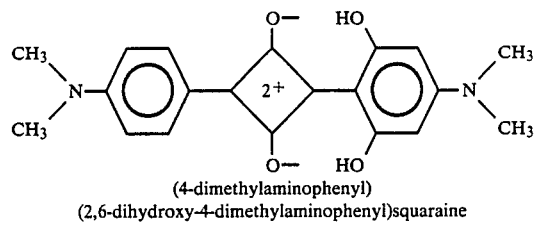

(4-dimethylaminophenyl)
(2,6-dihydroxy-4-dimethylaminophenyl)squaraine

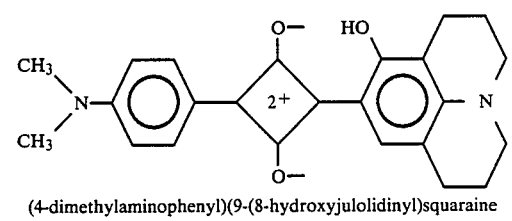

(4-dimethylaminophenyl)(9-(8-hydroxyjulolidinyl)squaraine

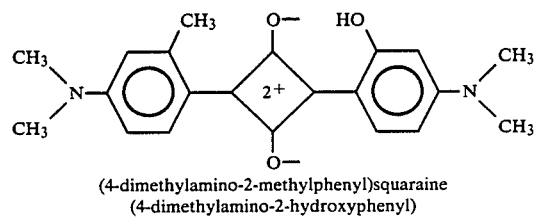

(4-dimethylamino-2-methylphenyl)squaraine
(4-dimethylamino-2-hydroxyphenyl)

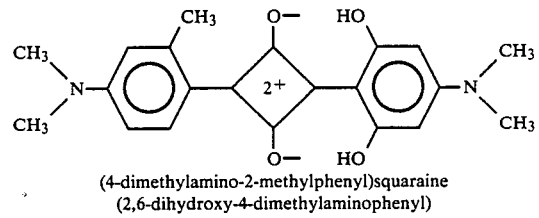

(4-dimethylamino-2-methylphenyl)squaraine
(2,6-dihydroxy-4-dimethylaminophenyl)

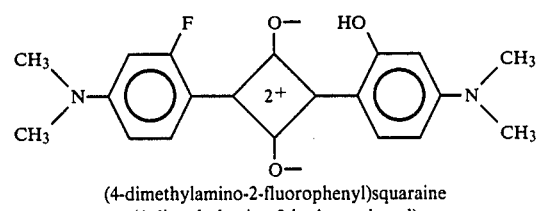

(4-dimethylamino-2-fluorophenyl)squaraine
(4-dimethylamino-2-hydroxyphenyl)

-continued

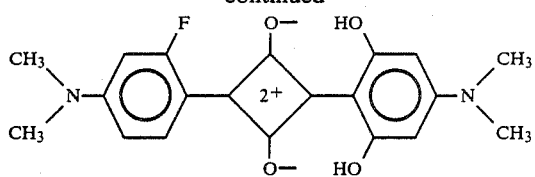
(4-dimethylamino-2-fluorophenyl)squaraine
(2,6-dihydroxy-4-dimethylaminophenyl)

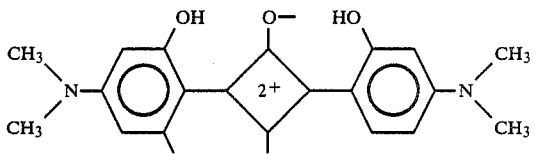
(2,6-dihydroxy-4-dimethylaminophenyl)squaraine
(4-dimethylamino-2-hydroxyphenyl)

The unsymmetrical squaraine compounds of the present invention can be prepared as illustrated herein with reference, for example, to method A; and/or method B. Accordingly, thus the unsymmetrical squaraine compounds of the present invention are generated by the initial preparation of an aryl cyclobutenedione intermediate, followed by the reaction thereof with a substituted aniline. With respect to method A, the aryl cyclobutenedione is prepared by heating with reflux at a temperature of from about 40° to about 50° C., depending on the solvent selected; about 20 millimoles to about 50 millimoles of a substituted aniline; from about 60 millimoles to about 150 millimoles of a dihalocyclobutenedione, especially dichlorocyclobutenedione; and from about 100 milliliters to about 1,000 milliliters of a Friedel Craft solvent inclusive of, for example, carbon disulfide, nitrobenzene, or methylene chloride. The aforementioned reaction is accomplished in the presence of a catalyst, for example, there is preferably selected from about 200 to about 900 millimoles of aluminum chloride. The reaction is allowed to continue for from about 4 to about 8 hours, and thereafter the Friedel Craft solvent is decanted therefrom. The resulting substituted aniline, reference the 4-(chloro cyclobutenedione) substituted aniline, from about 1 to about 50 millimoles is then reacted with from about 2 millimoles to about 100 millimoles of a hydroxy substituted aniline; and from about 10 to about 120 milliliters of an aliphatic alcoholic solvent, such as heptanol; and wherein the pressure is maintained at from about 10 Torr to about 760 Torr. Subsequent to separation, such as by filtration, there are obtained the squaraine compounds of the present invention, which are identified by the usual methods inclusive of infrared analysis, mass spectrometry, and NMR analysis. In further reference to method A, it is believed that the chloro cyclobutenedione converts to the hydroxy analog; and it is this analog that is reacted with the hydroxy substituted aniline.

In method B, there is initially reacted a dialkyl squarate, about 20 to about 100 millimoles, with from about 40 to about 200 millimoles of a trialkyloxonium salt, such as triethyloxonium fluoroborate; a halogenated solvent, such as methylene chloride, in an amount of from about 50 to about 150 milliliters; and a substituted aniline, from about 20 to 200 millimoles. This mixture was stirred at a temperature of from about 10° to about 40° C., and after further stirring for 1 hour at 15° to 35° C., the solvent was evaporated; and there was isolated an alkoxy cyclobutenedione intermediate, which was identified by infrared analysis, mass spectrometry and NMR analysis. This intermediate, reference the specific ethoxy compound illustrated in the method B scheme, was then hydrolyzed by heating in water at a temperature of from about 50° to about 100° C. for from about 1 hour to about 8 hours. Thereafter, from about 1 to about 50 millimoles of the resulting cyclobutenedione, specifically the 4(hydroxy cyclobutenedione) substituted aniline, is reacted with a hydroxy substituted aniline from about 2 to about 100 millimoles, in an alcoholic solvent, about 10 to about 120 milliliters, such as heptanol; and at a pressure of from about 10 Torr to about 760 Torr. There resulted, after separation, the squaraine compounds of the present invention; and yields, for example, of from about 40 to about 80 percent, which compounds were identified by infrared analysis, mass spectrometry, and NMR analysis.

Examples of specific reactants selected include aryl alkoxy cyclobutenediones, such as 4-phenyl-3-ethoxy cyclobutenedione, 4-(4-dimethylaminophenyl)-3-ethoxycyclobutenedione, 4-(4-dimethylamino-2-fluorophenyl)-3-ethoxy cyclobutenedione, 4-(4-dimethylamino-2-methylphenyl)-3-ethoxy cyclobutenedione, 4-(4-dimethylamino-2,6-dihydroxyphenyl)-3-ethoxy cyclobutenedione, 4-(4-methoxyphenyl)-3-ethoxy cyclobutenedione, 4-phenyl-3-methoxy cyclobutenedione, and 4-phenyl-3-butoxycyclobutenedione; aryl halo cyclobutenediones, such as 4-phenyl-3-chloro cyclobutenedione, 4-(4-dimethylaminophenyl)-3-chloro cyclobutenedione, 4-(4-dimethylamino-2-fluorophenyl)-3-chloro cyclobutenedione, 4-(4-dimethylamino-2-methylphenyl)-3-chloro cyclobutenedione, 4-(4-dimethylamino-2,6-dihydroxyphenyl)-3-chloro cyclobutenedione, 4-(4-methoxyphenyl)-3-chloro cyclobutenedione, 4-phenyl-3-bromo cyclobutenedione, 4-phenyl-3-iodo cyclobutenedione, and 4-phenyl-3-fluoro cyclobutenedione; aryl hydroxy cyclobutenediones, such as 4-phenyl-3-hydroxy cyclobutenedione, 4-(4-dimethylaminophenyl)-3-hydroxy cyclobutenedione, 4-(4-dimethylamino-2-fluorophenyl)-3-hydroxy cyclobutenedione, 4-(4-dimethylamino-2-methylphenyl)-3-hydroxy cyclobutenedione, 4-(4-dimethylamino-2,6-dihydroxyphenyl)-3-hydroxy cyclobutenedione, and 4-(4-methoxyphenyl)-3-hydroxy cyclobutenedione; and substituted anilines, such as N,N-dimethyl-3-hydroxy aniline, 8-hydroxyjulolidine, N,N-dimethyl-2,6-hydroxy aniline, N,N-dimethyl aniline, N,N-dimethyl-3-fluoro aniline, 8,10-dihydroxy julolidine, N,N-dimethyl-3-methyl aniline, and N-methyl-N-(4-chlorophenylmethyl)aniline.

The aforementioned reactions are illustrated with reference to the following equations:

Method A

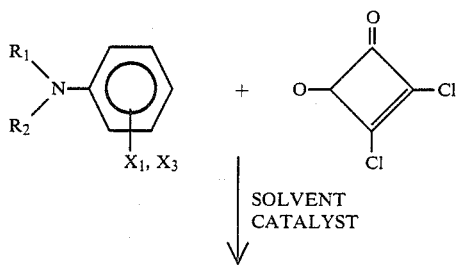

-continued
Method A

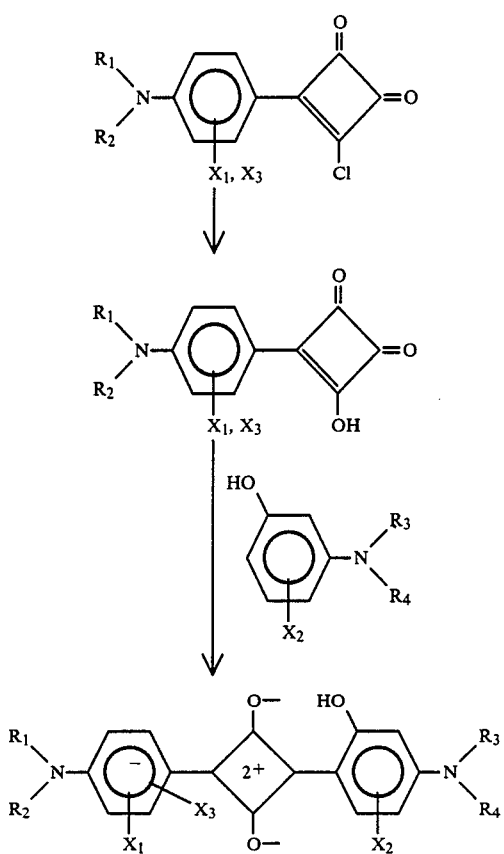

wherein the substituents $R_1$, $R_2$, $R_3$, $R_4$, $X_1$, $X_2$ and $X_3$ are as defined herein.

Method B

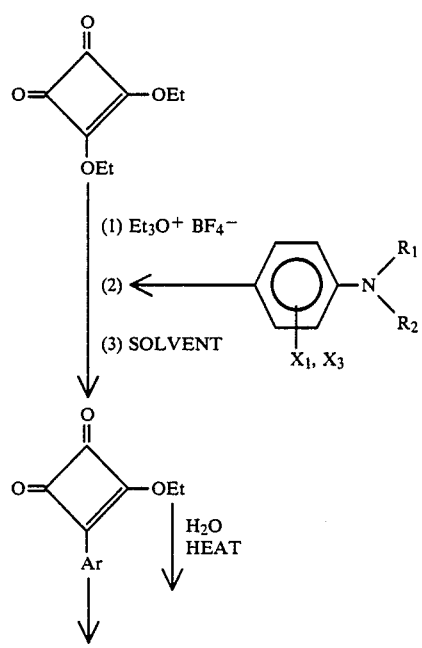

-continued
Method B

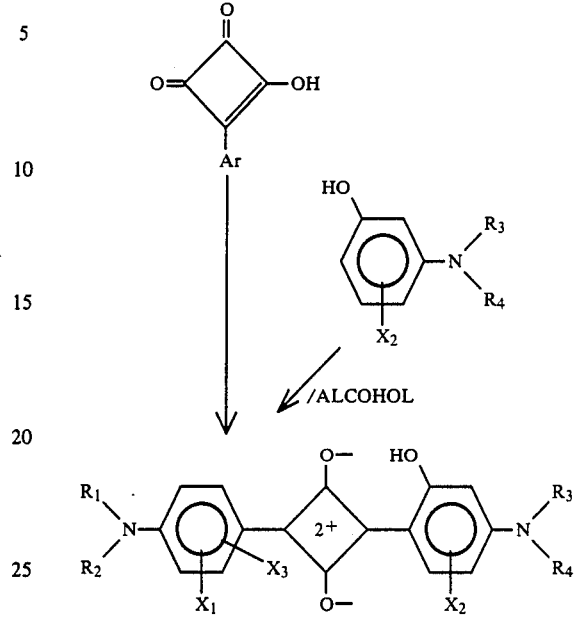

wherein Et is ethyl, Ar is the substituted aniline used in the initial reaction, $R_1$, $R_2$, $R_3$, $R_4$, $X_1$, $X_2$ and $X_3$ are as defined herein.

With respect to the photoresponsive imaging members, in one embodiment of the present invention they are comprised of a supporting substrate, an aryl amine hole transport layer, and as a photoconductive layer situated between the supporting substrate and the hole transport layer the unsymmetrical squaraine compounds of the present invention. There is also envisioned in accordance with the present layered photoresponsive imaging members comprised of a supporting substrate, a photoconductive layer comprised of one of the squaraine compounds of the present invention, and situated therebetween an aryl amine hole transport layer. Moreover, other imaging members also useful in printing processes are provided in accordance with the present invention, which imaging members can be comprised of a layer of a photoconductive composition situated between a photogenerating layer and an aryl amine hole transport layer; or wherein the photoconductive compound is situated between a photogenerating layer and the supporting substrate of such a member, the photoconductive compound comprised of one of the unsymmetrical squaraine compositions illustrated hereinbefore. Thus, a specific illustrative photoresponsive imaging member of the present invention is comprised of (1) a supporting substrate; (2) a hole blocking layer; (3) an optional adhesive interface layer; (4) an inorganic photogenerating layer; (5) a photoconductive layer comprised of one of the unsymmetrical squaraine compounds illustrated hereinbefore; and (6) an aryl amine hole transport layer. Alternatively, the photoconductive layer comprised of an unsymmetrical squaraine compound can be situated between the photogenerating layer and the supporting substrate. Therefore, in this variation, the photoresponsive imaging member of the present invention is comprised of (1) a supporting substrate; (2) a hole blocking layer; (3) an optional adhesive or adhesion interface layer; (4) a photoconductive layer containing one of the unsymmetrical squaraine compounds illustrated herein; (5) an inorganic photogenerating layer; and (6) an aryl amine hole transport layer. Exposure to illumination and erasure of the layered photoresponsive devices of the present invention may be accomplished from the front side, the rear side, or combinations thereof.

The improved photoresponsive devices of the present invention can be prepared by a number of known methods, the process parameters and the coating order of the layers being dependent on the device desired. Thus, for example, a three layered photoresponsive device can be prepared by a vacuum sublimation of the photoconducting layer on a supporting substrate, and subsequently depositing by solution coating the hole transport layer. In another process variant, the layered photoresponsive device can be prepared by providing the conductive substrate containing a hole blocking layer and an optional adhesive layer, and applying thereto by solvent coating processes, laminating processes, or other methods, a photogenerating layer, a photoconductive composition comprised of the novel squaraines of the present invention, and a hole transport layer.

In one specific preparation sequence, there is provided a 20 percent transmissive aluminized Mylar substrate of a thickness of about 3 mils (75 microns), which is coated by a ½ mil Bird applicator, with an adhesive, such as the adhesive available from E. I. DuPont as polyester 49,000 contained in a methylene chloride/trichloroethane solvent, or coated with silane hole blocking layer. Subsequently, there is applied to the adhesive layer a photoconductive layer comprised of an unsymmetrical squaraine of the present invention, which application is also accomplished with a Bird applicator with annealing at 135° C., followed by a coating of the amine transport layer. The amine transport layer is applied by known solution coating techniques, with a 5 mil Bird applicator and annealing at 135° C., wherein the solution comprises about 50 percent by weight of the amine transport molecule, and 50 percent by weight of a resinous binder substance such as a polycarbonate material.

The improved photoresponsive devices of the present invention can be incorporated into various imaging systems, such as those conventionally known as xerographic imaging processes. Additionally, the improved photoresponsive devices of the present invention including those containing an inorganic photogenerating layer, and a photoconductive layer comprised of the novel squaraines of the present invention can function simultaneously in imaging and printing systems with visible light and/or infrared light. In these embodiments, the improved photoresponsive devices of the present invention may be negatively charged, exposed to light in a wavelength of from about 400 to about 1,000 nanometers, either sequentially or simultaneously, followed by developing the resulting image and transferring to paper. The above sequence may be repeated many times.

BRIEF DESCRIPTION OF THE DRAWINGS

For a better understanding of the present invention and further features thereof reference is made to the following detailed description of various preferred embodiments wherein.

DESCRIPTION OF THE PREFERRED EMBODIMENTS

The preferred embodiments will now be illustrated with reference to specific photoresponsive imaging members comprised of the unsymmetrical squaraine compounds illustrated herein.

Figure 1:
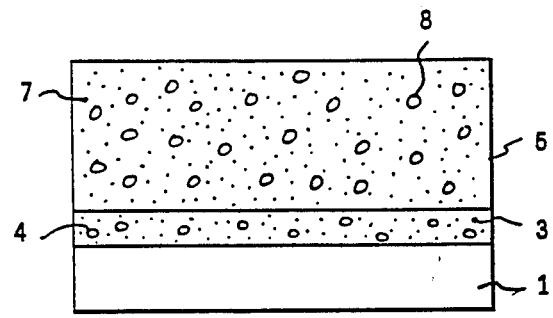
FIG. 1 is a partially schematic cross-sectional view of the photoresponsive imaging member of the present invention.

Illustrated in FIG. 1 is a photoresponsive imaging member of the present invention comprised of a supporting substrate 1 with an optional silane hole blocking layer thereover, a photoconductive layer 3 containing therein one of the unsymmetrical squaraine compounds illustrated hereinbefore, optionally dispersed in a resinous binder composition 4, and an aryl amine hole transport layer 5, comprised of hole transporting molecule 7 dispersed in an inactive resinous binder composition 8.

Figure 2:
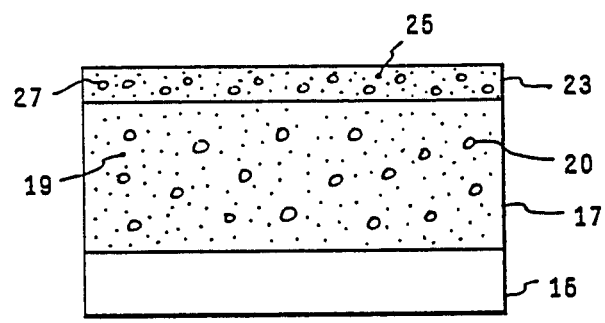
FIG. 2 is a partially schematic cross-section view of a further photoresponsive imaging member of the present invention.

In FIG. 2 there is illustrated essentially the same imaging member as described with reference to FIG. 1, with the exception that the aryl amine hole transport layer is situated between the supporting substrate and the photoconductive layer. More specifically, there is illustrated in FIG. 2 a photoresponsive imaging member comprised of a supporting substrate 15, a aryl amine hole transport layer 17 with hole transporting molecules 19 dispersed in an inert resinous binder composition 20, and a photoconductive layer 23 comprised of an unsymmetrical squaraine compound of the present invention 25, optionally dispersed in a resinous binder composition 27.

Figure 3:
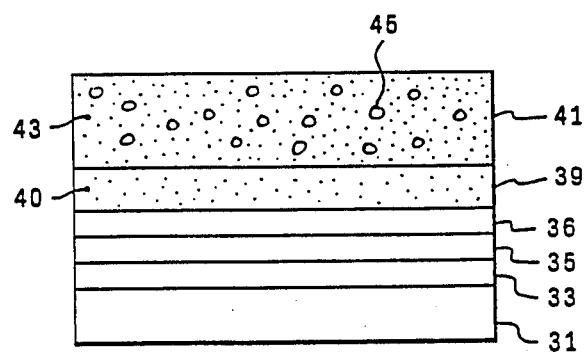
FIGS. 3 and 4 are partially schematic cross-sectional views of additional photoresponsive imaging members embraced by the present invention.

Illustrated in FIG. 3 is an improved photoresponsive imaging member of the present invention comprised of a supporting substrate 31, a hole blocking metal oxide, or a hole blocking silane layer 33; and an optional adhesive layer 35, a charge carrier inorganic photogenerating layer 36, an organic photoconductive layer 39 comprised of an unsymmetrical squaraine compound of the present invention 40; and capable of enhancing or reducing the intrinsic properties of the photogenerating layer 36 in the infrared or invisible range of the spectrum; and a charge carrier aryl amine hole transport layer 41 with aryl amine hole transporting molecules 43 dispersed in an inactive resinous binder 45.

Figure 4:
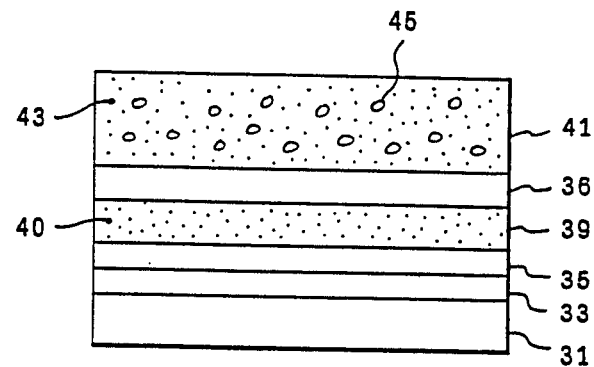

There is illustrated in FIG. 4 essentially the same imaging member as described with reference to FIG. 3 with the exception that the photoconductive layer with the unsymmetrical squaraine compound is situated between the inorganic photogenerating layer and the supporting substrate. More specifically, the photoconductive layer in the FIG. 4 embodiment is specifically situated between the optional adhesive layer 35 and the inorganic photogenerating layer 36.

Figure 5:
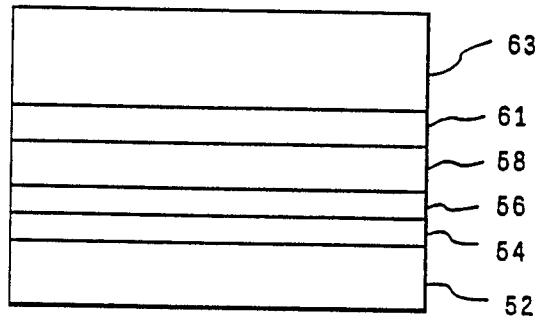
FIG. 5 is a partially schematic cross-sectional view of a further photoresponsive imaging member of the present invention.

Illustrated in FIG. 5 is a further photoresponsive imaging member of the present invention wherein the supporting substrate 52 is comprised of Mylar in a thickness of 3 mils (75 microns) containing a layer of 20 percent transmissive aluminum in a thickness of about 100 Angstroms, 0.01 micron; a metal oxide layer 54 comprised of aluminum oxide in a thickness of about 20 Angstroms; or a silane 0.1 micron in thickness; a polyester adhesive layer 56 commercially available from E. I. Dupont as 49,000 polyester, this layer being of a thickness of 0.5 micron; inorganic photogenerating layer 58 of a thickness of about 2.0 microns and comprised of 10 volume percent of $Na_2SeO_3$ and $Na_2CO_3$ doped trigonal selenium dispersed in a polyvinylcarbazole binder, 90 volume percent, a photoconductive layer 61 in a thickness of about 0.5 micron, and comprised of 30 volume percent of an unsymmetrical squaraine compound of the present invention dispersed in the resinous binder Formvar®, commercially available from Monsanto Chemical Company, 70 volume percent; and a hole transport layer 63 in a thickness of about 25 microns, comprised of 50 weight percent of N,N'-diphenyl-N,N'-bis(3-methylphenyl)-[1,1'-biphenyl]-4,4'-diamine dispersed in a polycarbonate resinous binder, 50 percent by weight.

With further reference to the Figures, the substrate layers may be opaque or substantially transparent, and can comprise any suitable material having the requisite mechanical properties. Thus, the substrate may comprise a layer of insulating material such as an inorganic or organic polymeric material, including Mylar a commercially available polymer; a layer of an organic or inorganic material having a semiconductive surface layer such as indium tin oxide, or aluminum arranged thereon, or a conductive material such as, for example, aluminum, chromium, nickel, brass or the like. The substrate may be flexible or rigid and many have a number of many different configurations, such as, for example a plate, a cylindrical drum, a scroll, an endless flexible belt and the like. Preferably, the substrate is in the form of an endless flexible belt. In some situations, it may be desirable to coat on the back of the substrate, particularly when the substrate is an organic polymeric material, an anticurl layer, such as for example polycarbonate materials commercially available as Makrolon.

The thickness of the substrate layer depends on many factors, including economical considerations, thus this layer may be of substantial thickness, for example, over 100 mils (2,500 microns); or of minimum thickness providing the objectives of the present invention are achieved. In one preferred embodiment, the thickness of the substrate is from about 3 mils (75 microns) to about 10 mils (250 microns).

The hole blocking layer can be comprised of various suitable known materials including aluminum oxide, silanes, reference U.S. Pat. No. 4,464,450, the disclosure of which is totally incorporated herein by reference, and the like. The preferred metal oxide layer is aluminum oxide. The primary purpose of this layer is to provide hole blocking, that is, to prevent hole injection from the substrate during and after charging. Typically, this layer is of a thickness of less than 50 Angstroms. Known adhesive layers, including polyesters, in a preferred thickness of 0.1 microns, are selected.

The inorganic photogenerating layer can be comprised of known photoconductive charge carrier generating materials sensitive to visible light, such as amorphous selenium, amorphous selenium alloys, halogen doped amorphous selenium, halogen doped amorphous selenium alloys, trigonal selenium, mixtures of Groups IA and IIA elements, selenite and carbonates with trigonal selenium, reference U.S. Pat. Nos. 4,232,102 and 4,223,283, the disclosure of each of these patents being totally incorporated herein by reference, cadmium sulfide, caldmium sulfur telluride, cadmium telluride, cadmium sulfur selenide, cadmium sulfur telluride, cadmium seleno telluride, copper, and chlorine doped cadmium sulfide, cadmium selenide and cadmium sulfur selenide and the like. Alloys of selenium included within the scope of the present invention include selenium tellurium alloys, selenium arsenic alloys, selenium tellurium arsenic alloys, and preferably such alloys containing a halogen material such as chlorine in an amount of from about 50 to about 200 parts per million.

Further, the photogenerating layer can also be comprised of organic materials including, for example, metal phthalocyanines, metal-free phthalocyanines, vanadyl phthalocynines and the like. Examples of many of these phthalocyanine substances are disclosed in U.S. Pat. No. 4,265,990, the disclosure of which is totally incorporated herein by reference. Preferred organic substances for the photogenerating layer include vanadyl phthalocyanine and x-metal-free phthalocyanine. This layer typically has a thickness of from about 0.05 microns to about 10 microns or more, and preferably is of a thickness from about 0.4 microns to about 3 microns; however, the thickness of this layer is primarily dependent on the photoconductive volume loading, which may vary from 5 to 100 volume percent. Generally, it is desirable to provide this layer in a thickness which is sufficient to absorb about 90 percent or more of the incident radiation which is directed upon it in the imagewise or printing exposure step. The maximum thickness of this layer is dependent primarily upon factors such as mechanical considerations, for example, whether a flexible photoresponsive device is desired.

A very important layer for the photoresponsive devices of the present invention is the photoconductive layer comprised of the novel squaraine compositions disclosed herein. These compositions, which are generally electronically compatible with the charge carrier transport layer, enable photoexcited charge carriers to travel in both directions across the interface between the photoconductive layer and the charge transport layer.

Generally, the thickness of the photoconductive layer depends on a number of factors including the thicknesses of the other layers, and the percent of photoconductive material contained therein. Accordingly, this layer can be of a thickness of from about 0.05 microns to about 10 microns, when the photoconductive squaraine composition is present in an amount of from about 5 percent to about 100 percent by volume; and preferably this layer is of a thickness of from about 0.25 microns to about 1 micron, when the photoconductive squaraine composition is present in this layer in an amount of 30 percent by volume. The maximum thickness of this layer is dependent primarily upon factors such as mechanical considerations, for example, whether a flexible photoresponsive device is desired.

The inorganic photogenerating materials or the photoconductive materials can comprise 100 percent of the respective layers, or these materials can be dispersed in various suitable inorganic or resinous polymer binder materials in amounts of from about 5 percent by volume to about 95 percent by volume, and preferably in amounts of from about 25 percent by volume to about 75 percent by volume. Illustrative examples of polymeric binder resinous materials that can be selected include those as disclosed, for example, in U.S. Pat. No. 3,121,006, the disclosure of which is totally incorporated herein by reference, polyesters, polyvinyl butyral, Formvar®, polycarbonate resins, polyvinyl carbazole, epoxy resins, phenoxy resins, especially the commercially available poly(hydroxyether) resins, and the like.

In one embodiment of the present invention, the charge carrier transport material, such as the diamine described hereinafter, may be incorporated into the photogenerating layer; or into the photoconductive layer in amounts, for example, of from about 1 volume percent of 60 volume percent.

The charge carrier transport layers, such as layer 14, can be comprised of a number of suitable materials which are capable of transporting holes, this layer generally having a thickness of from about 5 microns to about 50 microns, and preferably from about 20 microns to about 40 microns. In a preferred embodiment this transport layer comprises molecules of the formula:

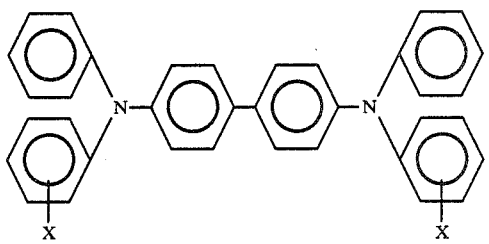

dispersed in a highly insulating and transparent organic resinous binder wherein X is selected from the group consisting of alkyl, and halogen, especially (ortho) $CH_3$, (meta) $CH_3$, (para) $CH_3$, (ortho) Cl, (meta) Cl, and (para) Cl.

Compounds corresponding to the above formula include, for example, N,N-diphenyl-N,N''-bis(alkylphenyl)-[1,1-biphenyl]-4,4'-diamines wherein alkyl is selected from the group consisting of methyl, such as 2-methyl, 3-methyl and 4-methyl, ethyl, propyl, butyl, hexyl and the like. With chloro substitution, the amine is N,N'-diphenyl-N,N'-bis(halo phenyl-[1,1-biphenyl]-4,4'-diamine wherein halo is 2-chloro, 3-chloro or 4-chloro.

Examples of the highly insulating and transparent resinous materials or inactive binder resinous material for the transport layers include substances such as those described in U.S. Pat. No. 3,121,006, the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight (Mw) of from about 20,000 to about 100,000, with a molecular weight in the range of from about 50,000 to about 100,000 being particularly preferred. Generally, the resinous binder contains from about 10 to about 75 percent by weight of the active material corresponding to the foregoing formula, and preferably from about 35 percent to about 50 percent of this material.

Also included within the scope of the present invention are methods of imaging with the photoresponsive imaging member illustrated herein. These methods of imaging generally involve the formation of an electrostatic latent image on the imaging member, followed by development image with known developer compositions, subsequently transferring the image to a suitable substrate and permanently affixing the image thereto. In those environments wherein the photoconductive member is to be used in a printing mode, the imaging method involves the same steps with the exception that the exposure step is accomplished with a laser device, or image bar rather than a broad spectrum white light source. In the latter embodiment, a photoresponsive imaging member is selected that is sensitive to infrared illumination.

The invention will not be described in detail with reference to specific preferred embodiments thereof, it being understood that these examples are intended to be illustrative only. The invention is not intended to be limited to the materials, conditions, or process parameters recited herein, it being noted that all parts and percentages are by weight unless otherwise indicated.

EXAMPLE I

There was prepared the unsymmetrical squaraine (4-dimethylaminophenyl) (2,6-dihydroxy-4-dimethylaminophenyl) squaraine by reacting 2.00 grams, 9.22 millimoles, of 4-(hydroxycyclobutenedione)-N,N-dimethylaniline with 1.25 grams, 9.25 millimoles, of N,N-dimethyl-m-toluidine in 37 milliliters of 1-heptanol. This reaction mixture was sealed in a flask, and the vacuum adjusted to enable the mixture to reflux at 107° C. upon heating. The reaction was allowed to continue for 6 hours, at which time refluxing was discontinued. Thereafter, the reaction mixture was permitted to cool to room temperature. Subsequently, there was separated by filtration 1.67 grams, 54 percent yield, a green crystalline product of the above squaraine as identified by mass spectrography M/z=334.

EXAMPLE II

There was prepared the unsymmetrical squaraine (4-dimethylaminophenyl) (2,6-dihydroxy-4-dimethylaminophenyl) squaraine by reacting 2.00 grams, 9.22 millimoles, of 4-(hydroxycyclobutenedione)-N,N-dimethylaniline with 1.44 grams, 9.40 millimoles, of 5-dimethylaminoresorcinol in 37 milliliters of 1-heptanol. This reaction mixture was sealed in a flask, and the vacuum adjusted to enable the mixture to reflux at 107° C. upon heating. The reaction was allowed to continue for 6 hours, at which time refluxing was discontinued. Thereafter, the reaction mixture was permitted to cool to room temperature. Subsequently, there was separated by filtration 2.50 grams, 77 percent yield, a green crystalline product of the above squaraine with a Lambda max of 622 in methylene chloride.

EXAMPLE III

There was prepared the unsymmetrical squaraine (4-dimethylaminophenyl) (4-dimethylamino-2-hydroxyphenyl squaraine by reacting 1.00 grams, 4.61 millimoles, of 4-(hydroxycyclobutenedione)-N,N-dimethylaniline with 635 milligrams, 4.63 millimoles, of 3-dimethylaminophenol in 18 milliliters of 1-heptanol. This reaction mixture was sealed in a flask, and the vacuum adjusted to enable the mixture to reflux at 107° C. upon heating. The reaction was allowed to continue for 5.5 hours, at which time refluxing was discontinued. Thereafter, the reaction mixture was permitted to cool to room temperature. Subsequently, there was separated by filtration 1.22 grams, 79 percent yield, a green crystalline product of the above squaraine, as identified by mass spectrography M/z=336, with a Lambda max of 632 in methylene chloride.

EXAMPLE IV

There was prepared the unsymmetrical squaraine (4-dimethylaminophenyl) (9-(8-hydroxycyclobutenedione)-N,N-dimethylaniline by reaction 1.00 grams, 4.61 millimoles, of 4-(hydroxycyclobutenedione)-N,N-dimethylaniline with 880 milligrams, 4.65 millimoles, of 8-hydroxyjulolidine in 21 milliliters of 1-heptanol. This reaction mixture was sealed in a flask, and the vacuum adjusted to enable the mixture to reflux at 107° C. upon heating. The reaction was allowed to continue for 6 hours, at which time refluxing was discontinued. Thereafter, the reaction mixture was permitted to cool to room temperature. Subsequently, there was separated by filtration 1.34 grams, 75 percent yield, a green crystalline product of the above squaraine, with a Lambda max of 632 in methylene chloride.

EXAMPLE V

The reactant 4-(chlorocyclobutenedione)-N,N-dimethylaniline was prepared by reacting 4.0 grams, 33 millimoles, of N,N-dimethylaniline with 15 grams, 99 millimoles, of dichlorocyclobutenedione and 40 grams, 300 millimoles, of $AlCl_3$ in 250 milliliters of $CS_2$. After 6 hours at reflux, the mixture was cooled to 15° C. and all of the $CS_2$ was decanted off. To the resulting solid at 0° was added ice water, and the product resulting was collected by filtration. After purification by column chromatography on silica gel (eluted with 25 percent $CH_2Cl_2$/75 percent toluene) the product, 2.6 grams, 33 percent yield, had a melting point of 190°-191°. This product had a lambda max of 410 nanometers in $CH_2Cl_2$, with a mass spectral analysis M/z 235.

EXAMPLE VI

The reactant 4-(ethoxycyclobutenedione)-N,N-dimethylaniline was prepared by reacting 10 grams, 59 millimoles, of diethylsquarate with 118 millimoles of triethyloxonium tetrafluoroborate in 118 milliliters of $CH_2Cl_2$ and then adding 7.1 grams, 59 millimoles, of N,N-dimethylaniline. After 1 hour the $CH_2Cl_2$ solution was washed with water and then concentrated by rotary evaporation. After purification by column chromatography on silica gel (eluted with 70 percent $CH_2Cl_2$/30 percent hexane) a bright yellow solid, 1.5 grams, 11 percent yield, was obtained. This product had a Lambda max of 390 nanometers in $CH_3CN$, with a mass spectral analysis M/z 245.

EXAMPLE VII

The reactant 4-(hydroxycyclobutenedione)-N,N-dimethylaniline with a melting point of greater than 350° C. was prepared by the hydrolysis of 4-(ethoxycyclobutenedione)-N,N-dimethylaniline, prepared in accordance with Example VI, at 70° C. in distilled water for one hour. This product had a mass spectral analysis M/z 217.

EXAMPLE VIII

A photoresponsive imaging member was prepared by providing a titanium metallized Mylar substrate in a thickness of 3 mils, followed by applying thereto with a multiple clearance film applicator, in a wet thickness of 0.5 mils, a hole blocking layer of N-methyl-3-aminopropyltrimethoxy silane, available from PCR Research Chemicals, Florida, in ethanol, in a 1:50 volume ratio. This layer was then allowed to dry for 10 minutes at room temperature, followed by curing for 10 minutes at 110° C. in a forced air oven.

A photoconductive layer containing 30 percent by weight of the (4-dimethylaminophenyl) (4-dimethylamino-2-hydroxyphenyl) squaraine prepared in accordance with Example III was then prepared as follows:

In a 2 ounce amber bottle there was added 0.15 grams of the squaraine, 0.35 grams of poly(vinylbutyral) resin available from Aldrich Chemicals; 72 grams of ⅛ inch stainless steel shot; and 10 grams of a methylene chloride/1,1,2-trichloroethane solvent mixture in a 3:2 weight ratio. The above mixture was placed on a ball mill for 22 hours.

The resulting slurry was then coated on the above substrate, with a multiple clearance film applicator, to a wet thickness of 1 mil. The layer was allowed to air dry for 30 minutes. This device was then dried at 135° C. for 15 minutes resulting in a dry thickness for the photoconductive layer of 0.9 microns.

There was then prepared a transport layer by mixing 65 percent by weight of Merlon M39 polycarbonate resin with 35 percent by weight N,N'-bis(3-methylphenyl)-1,1'-biphenyl-4,4'-diamine. The solution was then mixed to 9 percent by weight in methylene chloride. All of these components were then placed in an amber bottle and dissolved. The resulting mixture was coated to result in a layer with a dry thickness of 19 microns on top of the squaraine photoconductive or photogenerator layer, with a multiple clearance film applicator at a 10 mil wet gap thickness. The resulting imaging member was then air dried at room temperature for 1 hour, followed by drying in a forced air oven at 135° C. for 20 minutes.

EXAMPLE IX

A photoresponsive imaging member was prepared by repeating the procedure of Example VII with the exception that there was selected for the photoconductive layer (4-dimethylaminophenyl) (2,6-dihydroxy-4-(dimethylaminophenyl) squaraine as prepared in accordance with Example I.

EXAMPLE X

There was prepared a photoresponsive imaging member by repeating the procedure of Example VIII with the exception that there was selected for the photoconductive layer 30 percent by weight of (4-dimethylaminophenyl) (9-(8-hydroxyjulolidinyl) squaraine as prepared in accordance with Example V.

The imaging members as prepared in the above Examples were then tested for photosensitivity in the visible and infrared region of the spectrum by negatively charging the devices with corona to −800 volts, followed by simultaneously exposing each member to monochromic light to the wavelength region of about 400 to about 1,000 nanometers. The photoresponsive imaging members of Examples VIII to X responded to light in the wavelength region of 400 to 950 nanometers, indicating both visible and infrared photosensitivity.

The surface potential of each of the imaging members was also measured with an electrical probe after exposure to the given wavelengths, and the percent discharge of each member was then calculated, which discharge indicates photoresponse. Additionally, the imaging members as prepared in Examples VIII to X were tested for photosensitivity by charging each of the members in the dark to a surface potential of −800 volts, followed by measuring with an electrical probe the amount of light energy of monochromatic light supplied by a Xenon lamp in ergs/cm² required to discharge each imaging member to ½ of its surface potential.

Percent discharges and $E_{\frac{1}{2}}$ were then recorded for the imaging members as prepared in accordance with Examples VIII to X. More specifically, the percent discharge values for exposure to 10 ergs/cm² of 830 and 400 to 700 nanometers illumination were respectively 80 percent and 69 percent for the member of Example VIII, and 77 percent and 69 percent for the member of Example IX. These values indicate excellent infrared and visible photosensitivity. The percent discharge value for exposure to 10 ergs/cm² of 400 to 700 nanometers illumination for the imaging member of Example X was 36 percent.

Low values of $E_{\frac{1}{2}}$, that is for example below 100, indicate excellent photosensitivity for the imaging member involved.

The imaging members of Examples VIII and IX were characterized by the following $E_{\frac{1}{2}}$ values at 830 and 400 to 700 nanometers, respectively; 3 and 5 ergs/cm²; and 3.5 and 5 ergs/cm². The imaging members of Examples VIII and IX exhibited dark decay values of 79, and 105 volts per second, respectively. Also, the imaging member of Example X was characterized by an $E_{\frac{1}{2}}$ value of 26 ergs/cm² at 400 to 700 nanometers, while exhibiting a dark decay of 45 volts per second.

There were also prepared the following squaraines, and photoresponsive imaging members.

EXAMPLE XI

There was prepared the unsymmetrical squaraine (4-dimethylaminophenyl) (4-dimethylamino-2-fluorophenyl) squaraine by reacting 1.00 grams, 4.61 millimoles, of 4-(hydroxycyclobutenedione)-N,N-dimethylaniline with 0.813 grams, 5.84 millimoles, of N,N-dimethyl-3-fluoroaniline in 21 milliliters of 1-heptanol. This reaction mixture was sealed in a flask, and the vacuum adjusted so as to enable the mixture to reflux at 107° C. upon heating. The reaction was allowed to continue for 5.5 hours, at which time refluxing was discontinued. Thereafter, the reaction mixture was permitted to cool to room temperature. Subsequently, there was separated by filtration 812 milligrams, 52 percent yield, a green crystalline product of the above squaraine.

EXAMPLE XII

There was prepared the unsymmetrical squaraine (4-dimethylaminophenyl) (4-chlorophenylmethyl) methylaminophenyl squaraine by reacting 1.00 grams, 4.61 millimoles, of 4-(hydroxycyclobutenedione)-N,N-dimethylaniline with 1.07 grams, 4.62 millimoles, of methyl-(4-chlorophenylmethyl)aminobenzene in 18 milliliters of 1-heptanol. This reaction mixture was sealed in a flask, and the vacuum adjusted to enable the mixture to reflux at 107° C. upon heating. The reaction was allowed to continue for 5 hours, at which time refluxing was discontinued. Thereafter, the reaction mixture was permitted to cool to room temperature. Subsequently, there was separated by filtration 817 milligrams, 41 percent yield, a green crystalline product of the above squaraine.

EXAMPLE XIII

There was prepared the unsymmetrical squaraine (4-dimethylaminophenyl) (4-dimethylamino-2-methylphenyl) squaraine by reacting 1.00 gram, 4.25 millimoles, of 4-(chlorocyclobutenedione)-N,N-dimethylaniline with 574 milligrams, 4.25 millimoles, of N,N-dimethyl-m-toluidine in 20 milliliters of 1-heptanol. This reaction mixture was sealed in a flask, and the vacuum adjusted so as to enable the mixture to reflux at 107° C. upon heating. The reaction was allowed to continue for 5.5 hours, at which time refluxing was discontinued. Thereafter, the reaction mixture was permitted to cool to room temperature. Subsequently, there was separated by filtration 70 milligrams, 5 percent yield, a green crystalline product of the above squaraine.

EXAMPLE XIV

A photoresponsive imaging member was prepared by repeating the procedure of Example VIII with the exception that there was selected for the photoconductive layer 30 percent by weight of (4-dimethylaminophenyl) (4-dimethylamino-2-fluorophenyl) squaraine as prepared in accordance with Example XI.

EXAMPLE XV

A photoresponsive imaging member was prepared by repeating the procedure of Example VIII with the exception that there was selected for the photoconductive layer 30 percent by weight of (4-dimethylaminophenyl) (4-chlorobenzylmethyl-aminophenyl) squaraine as prepared in accordance with Example XII.

EXAMPLE XVI

There was prepared a photoresponsive imaging member by repeating the procedure of Example VIII with the exception that there was selected for the photoconductive layer 30 percent by weight of (4-dimethylaminophenyl) (4-dimethylamino-2-methylphenyl) squaraine as prepared in accordance with Example XII.

Although the invention has been described with reference to specific preferred embodiments, it is not intended to be limited thereto, rather those skilled in the art will recognize variations and modifications may be made therein which are within the spirit of the present invention and within the scope of the following claims.

What is claimed is:

1. Unsymmetrical squaraine compounds of the following formula

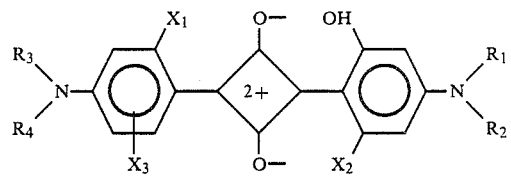

wherein $R_1$, $R_2$, $R_3$ and $R_4$ are independently selected from the group consisting of alkyl, aryl, heterocyclic, benzyl, and halobenzyl; $X_2$ is independently selected from the group consisting of hydrogen, alkyl, halogen, carboxy, and hydroxy; and $X_1$ and $Z_3$ are independently selected from the group consisting of hydrogen, alkyl, halogen, and carboxy, subject to the provision that $X_2$ and $X_3$ represent different substituents.

2. A squaraine compound in accordance with claim 1 wherein alkyl is from 1 to about 20 carbon atoms.

3. A squaraine compound in accordance with claim 1 wherein alkyl is from 1 to about 6 carbon atoms.

4. A squaraine compound in accordance with claim 1 wherein alkyl is methyl.

5. A squaraine compound in accordance with claim 1 wherein aryl is from 6 to about 24 carbon atoms.

6. A squaraine compound in accordance with claim 1 wherein aryl is phenyl.

7. A squaraine compound in accordance with claim 1 wherein the halobenzyl is fluorobenzyl.

8. A squaraine compound in accordance with claim 1 wherein the halogen for $X_1$, $X_2$ and $X_3$ are selected from the group consisting of chloride and fluoride.

9. The unsymmetrical squaraine compound (4-dimethylaminophenyl) (4-dimethylamino-2-hydroxyphenyl)squaraine.

10. The unsymmetrical squaraine compound (4-dimethylaminophenyl) (2,6-dihydroxy-4-dimethylaminophenyl)squaraine.

11. The unsymmetrical squaraine compound (4-dimethylaminophenyl) (9-(8-hydroxyjulolidinyl)squaraine.

12. The unsymmetrical squaraine compound (4-dimethylamino-2-methylphenyl) (4-dimethylamino-2-hydroxyphenyl)squaraine.

13. The unsymmetrical squaraine compound (4-dimethylamino-2-methylphenyl) (2,6-dihydroxy-4-dimethylaminophenyl)squaraine.

14. The unsymmetrical squaraine compound (4-dimethylamino-2-fluorophenyl) (4-methylamino-2-hydroxyphenyl)squaraine.

15. The unsymmetrical squaraine compound (4-dimethylamino-2-fluorophenyl) (2,6-dihydroxy-4-dimethylaminophenyl)squaraine.

16. The unsymmetrical squaraine compound (2,6-dihydroxy-4-dimethylaminophenyl) (4-dimethylamino-2-hydroxyphenyl)squaraine.

* * * * *